(12) United States Patent
Nomura et al.

(10) Patent No.: US 8,501,974 B2
(45) Date of Patent: Aug. 6, 2013

(54) PROCESS FOR PRODUCING ALKYL FATTY ESTERS

(75) Inventors: Wataru Nomura, Wakayama (JP);
Nobuhiro Tatsumi, Wakayama (JP);
Takanobu Katayama, Wakayama (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 12/158,833

(22) PCT Filed: Dec. 26, 2006

(86) PCT No.: PCT/JP2006/326329
§ 371 (c)(1),
(2), (4) Date: Jun. 23, 2008

(87) PCT Pub. No.: WO2007/077950
PCT Pub. Date: Jul. 12, 2007

(65) Prior Publication Data
US 2009/0105492 A1 Apr. 23, 2009

(30) Foreign Application Priority Data
Dec. 28, 2005 (JP) ................................. 2005-378698

(51) Int. Cl.
*C11C 3/00* (2006.01)
(52) U.S. Cl.
USPC ............................ 554/169; 554/124; 554/170
(58) Field of Classification Search
USPC .................................................. 554/124, 170
See application file for complete search history.

(56) References Cited

U.S. PATENT DOCUMENTS

| 5,157,168 | A | 10/1992 | Wilmott et al. |
| 6,383,970 | B1* | 5/2002 | Mimura et al. ............. 502/162 |
| 2004/0034244 | A1 | 2/2004 | Bournay et al. |
| 2004/0133049 | A1 | 7/2004 | Pelzer et al. |
| 2005/0113588 | A1* | 5/2005 | Hillion et al. .............. 554/174 |
| 2005/0204612 | A1 | 9/2005 | Connemann et al. |

FOREIGN PATENT DOCUMENTS

| EP | 1 211 236 | 6/2002 |
| EP | 1 460 124 | 9/2004 |
| GB | 795 573 | 5/1958 |
| JP | 56 65097 | 6/1981 |
| JP | 61 254255 | 11/1986 |
| JP | 6-313188 | 11/1994 |
| JP | 2001-79413 | 3/2001 |
| JP | 2002-155027 | 5/2002 |
| JP | 2003 246997 | 9/2003 |
| JP | 2004 27170 | 1/2004 |
| WO | WO 2004/029016 A1 * | 4/2004 |

OTHER PUBLICATIONS

Office Action issued May 24, 2011 in Japan Application No. 2005-378698 (With English Translation).
Office Action issued Feb. 7, 2012, in Japanese Patent Application No. 2005-378698 (with English-language translation).

* cited by examiner

*Primary Examiner* — Yate K Cutliff
(74) *Attorney, Agent, or Firm* — Oblon, Spivak, McClelland, Maier & Neustadt, L.L.P.

(57) ABSTRACT

Disclosed is a process for producing alkyl fatty esters from fats/oils and C1 to C5 lower alcohols by a multistage reaction process, which includes feeding fats and oils to a reactor at an upper stage and then sent to a stage at the downstream side while feeding lower alcohols to a reactor at a lower stage, and simultaneously returning lower alcohols recovered from an outlet of the reactor to a stage at the upstream side, thereby repeating the reaction.

10 Claims, 1 Drawing Sheet

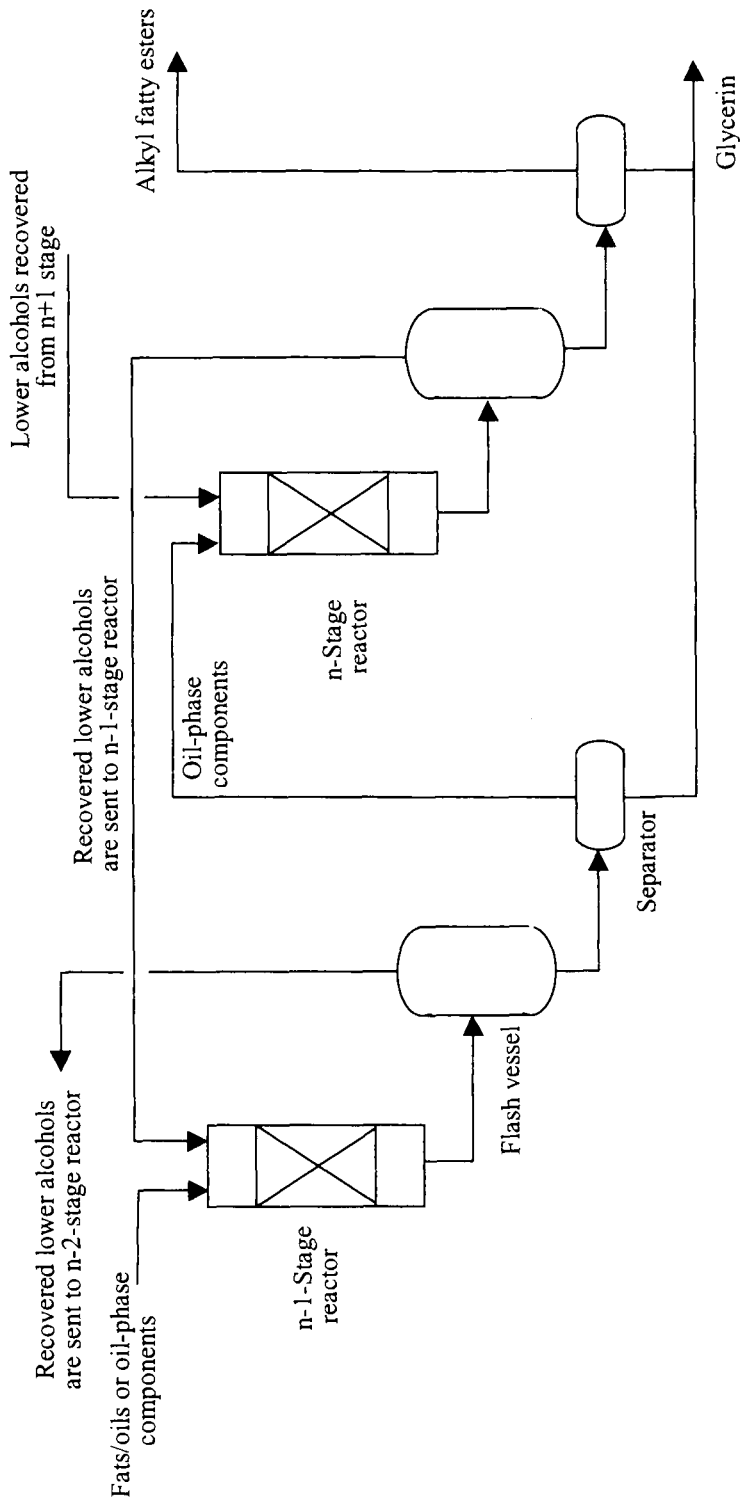

PROCESS FOR PRODUCING ALKYL FATTY ESTERS

FIELD OF THE INVENTION

The present invention relates to a process for producing alkyl fatty esters from fats/oils and lower alcohols.

BACKGROUND OF THE INVENTION

Fats and oils (hereinafter referred to sometimes as fats/oils) contain esters called triglycerides as the main raw material, and alkyl fatty esters are produced from fats and oils by ester exchange with alcohols. Particularly, alkyl fatty esters produced from vegetable oils are regarded as important biodiesel fuel oil not increasing carbon dioxide, from the viewpoint of countermeasures against global warming. High-quality standards are established for alkyl fatty esters as biodiesel fuel oil, and in Europe, the acid value of alkyl fatty esters is established to be not higher than 0.5 mg KOH/g. That is, it is required to produce high-quality alkyl fatty esters. It is further desired to use alkyl fatty esters of low acid value in production of fatty alcohols from alkyl fatty esters.

As processes for producing alkyl fatty esters from fats/oils and alcohols, various processes are known. In this reaction, for example, JP-A 2004-27170 describes that raw materials are reacted in the presence of an alkali catalyst after removal of water from raw oils by a water-absorbing filter. With respect to an acid catalyst, JP-A 2003-246997 makes use of sulfuric acid, hydrochloric acid etc.

On one hand, JP-A56-65097 describes a multistage process wherein prior to reaction, glycerin is separated and then crude esters are fed to a next stage. In JP-A 61-254255, alcohols are first evaporated from a reaction mixture and then unreacted materials are refluxed while glycerin is removed by phase separation.

SUMMARY OF THE INVENTION

The present invention provides a process for producing alkyl fatty esters from fats/oils and a C1 to C5 lower alcohol(s) by a multistage reaction process, which includes feeding fats and oils to a reactor at an upper stage and then sent to a stage at the downstream side while feeding lower alcohols to a reactor at a lower stage, and simultaneously returning lower alcohols recovered from an outlet of the reactor to a stage at the upstream side, thereby repeating the reaction.

The present invention provides a process for producing fatty alcohols from hydrogen and the alkyl fatty esters obtained by the process described above.

DETAILED DESCRIPTION OF THE INVENTION

In JP-A 2004-27170 and JP-A 2003-246997, the catalyst is a homogeneous catalyst, thus necessitating a step of neutralization/removal of the catalyst after the ester-exchange reaction.

JP-A 56-65097 does not refer to recovery of unreacted alcohols. JP-A 61-254255 uses not multistage reaction but a circulating process using a powdery catalyst and is thus estimated to have a problem with the quality of alkyl fatty esters.

The present invention provides a process for producing alkyl fatty esters of low acid value in higher yield from fats/oils and lower alcohols by a multistage reaction process.

According to the present invention, remaining glycerides can be reduced to an extremely low concentration, and alkyl fatty esters of low acid value can be produced economically advantageously in higher yield. When lower alcohols are fed successively to an upper stage as is the case with fats and oils, as opposed to the process of the invention, the concentration of water in the lower alcohols becomes high, thus reducing the reaction rate and increasing the acid value of alkyl fatty esters.

In the invention, lower alcohols are effectively recovered while the quality of alkyl fatty esters is secured.

The fats and oils used in the present invention include naturally occurring vegetable fats and oils and animal fats and oils. The vegetable fats and oils include coconut oil, palm oil, palm kernel oil etc., and the animal fats and oils include tallow, lard, fish oil etc.

Specific examples of the C1 to C5 lower alcohols used in the present invention include methanol, ethanol, propanol etc., among which methanol is preferable from the viewpoint of low cost and easy recovery.

A fixed-bed reactor packed with a solid catalyst is preferably used as the reactor in the present invention. The solid catalyst is preferably a solid acid catalyst, more preferably a weakly acidic solid acid catalyst having a strong acid point of not higher than 0.2 mmol/g-cat and a weak acid point of not lower than 0.3 mmol/g-cat, each acid point being defined as follows:

Weak acid point: the point at which desorption of $NH_3$ occurs in the range of 100 to 250° C. in TPD (temperature programmed desorption: ammonia adsorption-desorption process)

Strong acid point: the point at which desorption of $NH_3$ occurs in the range of higher than 250° C. in TPD It is further preferable that the weakly acidic solid catalyst is a molded product of a solid catalyst having the structure (A), the structure (B) and the metal atom (C) as follows:

Structure (A): a structure of an inorganic phosphoric acid wherein the hydrogen atom is removed from at least one OH group thereof, Structure (B): a structure of an organic phosphoric acid represented by the general formula (1) or (2) below, wherein the hydrogen atom is removed from at least one OH group thereof:

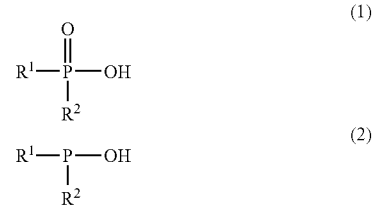

wherein —$R^1$ and —$R^2$ each represent a group selected from —R, —OR, —OH and —H, and at least one of —$R^1$ and —$R^2$ is —R or —OR provided that R is a C1 to C22 organic group.

Metal atom (C): one or more metal atom selected from the group consisting of aluminum, gallium and iron.

In the structure (A) above, the inorganic phosphoric acid includes orthophosphoric acid or condensed phosphoric acids such as metaphosphoric acid or pyrophosphoric acid, among which orthophosphoric acid is preferable in respect of property. In the structure (B), the organic phosphoric acid represented by the general formula (1) or (2) includes phosphonic acid, monophosphonate, phosphinic acid, monophosphate, diphosphate, monophosphite and diphosphite or a mixture thereof, preferably phosphonic acid.

The organic group R of the organic phosphoric acid is preferably an alkyl group such as methyl, ethyl, n-propyl, iso-propyl, n-butyl, iso-butyl, tert-butyl, n-hexyl, 2-ethylhexyl, octyl, dodecyl or octadecyl or an aryl group such as phenyl and 3-methylphenyl. Further an amino group, an alkoxy group, a carbonyl group, an alkoxycarbonyl group, a carboxylic acid group, a halogen atom such as chlorine, a phosphonic acid group or a sulfonic acid group may be added to the above shown example of the organic group of R.

From the viewpoint of performance and/or cost, the metal atom (C) is preferably aluminum. For the purpose of improving selectivity and other properties, the metal atom (C) may contain a small amount of metal atoms other than aluminum, gallium and iron. It is not always necessary that all metal atoms (C) contained in the catalyst are bonded to the structure (A) or (B), and therefore, a part of the metal atoms (C) may be present in the form of metal oxide, metal hydroxide etc.

Another preferable example of the weakly acidic solid acid catalyst of the invention is a molded, heterogeneous catalyst containing aluminum orthophosphate, preferably having a pore diameter of 6 to 100 nm, a pore capacity of 0.46 ml/g or more, and an acid content of 0.40 mmol/g or more.

The process for producing the weakly acidic solid acid catalyst in the present invention includes a precipitation method, a method of impregnating a metal oxide or hydroxide with organic and inorganic phosphoric acids, and a method of replacing an inorganic phosphoric acid group of an inorganic aluminum phosphate gel by an organic phosphoric acid group, among which the precipitation method is preferable.

In preparing the solid catalyst of the present invention, a support having a large surface area may coexist to obtain a catalyst supported thereon. As the support, use can be made of silica, alumina, silica alumina, titania, zirconia, diatomaceous earth, activated carbon etc. When the support is used in excess, the content of the active component is decreased and in consequence the activity is lowered, and thus the proportion of the support in the catalyst is preferably not higher than 90 wt %.

In the mode of reaction in the invention, it is possible to use either a vessel type reactor having a stirrer or a fixed-bed reactor packed with a catalyst, and the fixed-bed reactor is preferable from the viewpoint of eliminating the necessity for separation of the catalyst. When the reaction is continuously carried out in a fixed-bed reactor, the liquid hourly space velocity (LHSV) based on the fats and oils is preferably not lower than 0.02/hr, more preferably not lower than 0.1/hr, from the viewpoint of increasing productivity per unit volume of the reactor to effect the reaction economically. From the viewpoint of attaining a sufficient reaction rate, the LHSV is preferably not higher than 2.0/hr, more preferably not higher than 1.0/hr.

The reaction system of the fixed-bed reaction may be the reaction of 3 phases, that is, liquid (alcohols)/liquid (fats and oils)/solid (catalyst) where the lower alcohols such as methanol are contacted in a liquid state or gas (alcohols)/liquid (fats and oils)/solid (catalyst) wherein the lower alcohols have been gasified. In the reaction in the liquid/liquid/solid system, a mixture of the two liquids may be allowed to flow upward or downward and thereby contacted with each other. In the reaction in the gas/liquid/solid system, they may be contacted with one another in either a gas-liquid co-current system or a gas-liquid countercurrent system.

In the present invention, reactors preferably fixed-bed reactors each packed with a solid catalyst are arranged at multi-stages, and fats and oils are fed to a reactor at an upper stage, preferably at the uppermost stage and then sent to a stage at the downstream side preferably one after another while feeding lower alcohols to a reactor at a lower stage, preferably at the lowermost stage, and simultaneously returning lower alcohols recovered from an outlet of the reactor to a stage at the upstream side preferably one after another, thereby repeating the reaction. As used herein, "the upstream side" refers to a side nearer to the fixed-bed reactor to which starting fats and oils are first fed, while "the uppermost stage" refers to a stage at the uppermost side.

In the process of the present invention, the direction of the flow of liquid in each reactor may be either a downflow or an upflow, preferably a downflow. In the case of the downflow as shown in FIG. 1, a plurality of fixed-bed reactors each packed with a solid catalyst are arranged at multi-stages in series, and fats and oils are fed to a reactor at an upper stage, preferably at the uppermost stage and then sent to lower stages preferably one after another, while lower alcohols are fed to the top of a reactor at a lower stage, preferably at the lowermost stage and contacted with the liquid (fats and oils) from an upper stage, and then lower alcohols after separation are fed to the top of a reactor at an upper stage and contacted with fats and oils in the same manner as above. In this embodiment, therefore, the lower alcohols to be fed can be reduced economically advantageously and simultaneously the amount of remaining fats and oils can be reduced. If lower alcohols are fed to a reactor at an upper stage, the content of water in methanol becomes high, thus reducing the reaction rate and increasing the acid value of the esters; however, the process of the invention is free of such disadvantage because lower alcohols are fed to a reactor at a lower stage.

The process preferably includes a step wherein lower alcohols are separated from a reaction mixture containing fats and oils obtained from a reactor at an upper stage and the resulting liquid component is subjected to oil/water separation to remove glycerin, between the reactor at an upper stage and the reactor at a lower stage.

From the viewpoint of attaining an excellent reaction rate, the necessary stoichiometric quantity of lower alcohols, in terms of the molar ratio of lower alcohols to fats and oils (calculated as triglycerides), is preferably 1.5 or more, more preferably 2 or more. From the viewpoint of effecting the reaction economically by reducing the amount of lower alcohols recovered, the molar ratio of lower alcohols to fats and oils is preferably 50 or less, more preferably 30 or less, even more preferably 15 or less. If necessary, the fats and oils may be diluted with a diluent. The diluent includes, but is not limited to, xylene, toluene, hexane, tetrahydrofuran, acetone, ether, and alkyl fatty esters.

The reaction temperature is preferably 50° C. or more, more preferably 60° C. or more, even more preferably 80° C. or more, from the viewpoint of attaining a sufficient catalyst activity to increase the reaction rate and of effecting the reaction economically by controlling the necessary volume of a reactor for attaining the desired rate of reaction. The reaction temperature is preferably 220° C. or less, more preferably 200° C. or less, from the viewpoint of inhibiting the formation of ethers as byproducts between glycerin such as methoxypropanediol and lower alcohols thereby preventing the glycerin purifying step from being complicated.

The reaction time varies depending on the reaction conditions (for example, reaction mode, catalyst amount, temperature), but in the reaction in a vessel type reactor, the reaction time may be usually 2 to 10 hours. In the continuous reaction in a fixed-bed reactor, the liquid hourly space velocity (LHSV) of the fats and oils is set preferably at 0.02 to 2.0/hr as described above.

The reaction pressure is preferably 0.1 to 10 MPa, more preferably 0.5 to 8 MPa. When the reaction in the liquid/ liquid/solid system is carried out, the reaction temperature and pressure are established on the basis of the vapor pressure of the alcohols.

The reaction products obtained in the manner described above contain glycerin and lower alcohols in addition to the desired alkyl fatty esters. These lower alcohols can be separated in a usual manner by evaporation from the reaction products discharged from the outlet of the fixed-bed reactor, and the glycerin can be separated by leaving the reaction mixture, whereby the desired alkyl fatty esters can be isolated.

[Process for Producing Fatty Alcohols]

The process for producing fatty alcohols according to the present invention is a process wherein the alkyl fatty esters obtained by the above-described process of the invention are subjected to hydrogenation reaction to give fatty alcohols. As used herein, the fatty alcohols refer to alcohols derived from fats and oils.

In this process, the hydrogenation catalyst used can be a generally known copper-based catalyst or a noble metal-based catalyst such as catalysts based on palladium or platinum. The copper catalyst can include catalysts such as those made of copper-chrome, copper-zinc, copper-iron-aluminum, copper-silica, etc.

The hydrogenation reaction can be carried out in the presence of a hydrogenation catalyst in any generally used reaction systems such as a fluidized bed system or a fixed bed system.

When the hydrogenation reaction is carried out in a fluidized bed system, the amount of the hydrogenation catalyst can be selected arbitrarily in such a range as to achieve practical reaction yield, depending on reaction temperature and reaction pressure, but preferably the amount of the catalyst is 0.1 to 20 wt % based on the alkyl fatty esters. The reaction temperature is preferably 160 to 350° C., more preferably 200 to 280° C. The reaction pressure is preferably 0.1 to 35 MPa, preferably 3 to 30 MPa.

When the hydrogenation reaction is continuously carried out in a fixed bed system, the hydrogenation catalyst is molded preferably in a cylindrical, pellet or spherical form. The reaction temperature is preferably 130 to 300° C., more preferably 150 to 270° C., and the reaction pressure is preferably 0.1 to 30 MPa. In consideration of productivity and reactivity, the LHSV can be determined arbitrarily depending on the reaction conditions.

BRIEF DESCRIPTION OF THE DRAWING

FIG. 1 is a diagrammatic illustration showing the preferable production process of the present invention.

EXAMPLES

The present invention is described in more detail by reference to the Examples. The Examples are illustrative of the present invention and not intended to limit the present invention.

Catalyst Production Example 1

9.9 g ethylphosphonic acid, 27.7 g of 85% orthophosphoric acid, and 112.5 g aluminum nitrate.9H$_2$O were dissolved in 1000 g water. Aqueous ammonia was added dropwise to this mixed solution at room temperature until the pH was increased to 5. During this step, gelled white precipitates were formed. The precipitates were filtered off, washed with water, dried at 110° C. for 15 hours and pulverized to a size of 60-mesh or less. Alumina sol was added in a final content of 10% to the pulverized catalyst, and the catalyst was extrusion-molded into 1.5-mmφ pieces. These pieces were calcinated at 250° C. for 3 hours to give a molded catalyst consisting of a solid acid catalyst (referred to hereinafter as catalyst 1). The weak acid point of the resulting catalyst was 1 mmol/g, and the strong acid point was below the limit of detection.

Reference Example 1

Two tube reactors each having an inner diameter of 35.5 mmφ and a length of 800 mmH, having a tube of 6 mm in inner diameter for temperature measurement in the axial direction, were connected in series and each tube was packed with 450 cc catalyst 1. Refined palm kernel oil having an acid value of 0.1 was used as the fats and oils and fed together with commercial methanol (water content 0.15 wt %; commercial methanol used hereinafter refers to this commercial methanol) into the top of the reactor and reacted with one another. The fats and oils were fed such that the LHSV became 0.4. The molar amount of methanol fed was 10 times as much as the molar amount of the fats and oils fed. The reaction pressure was 3.0 MPa·G, and the reaction temperature was 170° C. As a result of analysis of the resulting reaction products, the degree of formation of the methyl fatty ester in the oil phase was 87.0%, and the acid value of the oil phase was 0.74 (mg KOH/g).

Reference Example 2

A tube reactor having an inner diameter of 237.2 mmφ and a length of 1020 mmH was packed with 45000 cc catalyst 1. Refined palm kernel oil having an acid value of 0.1 was used as the fats and oils and fed together with commercial methanol into the top of the reactor and reacted with one another. The fats and oils were fed such that the LHSV became 0.4. The molar amount of methanol fed was 10 times as much as the molar amount of the fats and oils fed. The reaction pressure was 3.0 MPa·G, and the reaction temperature was 180° C. After unreacted methanol was recovered by evaporation from the resulting reaction products, the reaction mixture was left to separate it into oil and glycerin phases and each phase was recovered. As a result of analysis of the reaction products, the degree of formation of the methyl fatty ester in the oil phase was 83.2%.

Example 1

Operation 1: Two tube reactors each having an inner diameter of 35.5 mmφ and a length of 800 mmH, having a tube of 6 mm in inner diameter for temperature measurement in the axial direction, were connected in series and each tube was packed with 350 cc catalyst 1. The oil containing 85.6% methyl fatty ester, obtained by leaving the reaction mixture in Reference Example 2, was used and fed together with commercial methanol into the top of the reactor and reacted with one another. The fats and oils were fed such that the LHSV became 0.8. The molar amount of methanol fed was 10 times as much as the molar amount of the fats and oils fed. The reaction pressure was 3.0 MPa·G, and the reaction temperature was 170° C. As a result of analysis of the resulting reaction products, the degree of formation of the methyl fatty ester in the oil phase was 98.2%, and the acid value of the oil phase was 0.23 (mg KOH/g). Unreacted methanol was recovered by evaporation from the resulting reaction mixture.

Operation 2: Two tube reactors each having an inner diameter of 35.5 mm⌀ and a length of 800 mmH, having a tube of 6 mm in inner diameter for temperature measurement in the axial direction, were connected in series and each tube was packed with 450 cc catalyst 1. Refined palm kernel oil having an acid value of 0.1 was used as the fats and oils and fed together with the unreacted methanol (water content, 1.1 wt %) recovered in the operation 1 into the top of the reactor and reacted with one another. The fats and oils were fed such that the LHSV became 0.4. The molar amount of methanol fed was 10 times as much as the molar amount of the fats and oils fed. The reaction pressure was 3.0 MPa·G, and the reaction temperature was 170° C. As a result of analysis of the resulting reaction products, the degree of formation of the methyl fatty ester in the oil phase was 86.9%, and the acid value of the oil phase was 0.86 (mg KOH/g).

Comparative Example 1

Two tube reactors each having an inner diameter of 35.5 mm⌀ and a length of 800 mmH, having a tube of 6 mm in inner diameter for temperature measurement in the axial direction, were connected in series and each tube was packed with 350 cc catalyst 1. The oil containing 85.6% methyl fatty ester, obtained by leaving the reaction mixture in Reference Example 2, was used and fed together with the unreacted methanol (water content, 1.1 wt %) recovered in Reference Example 2 into the top of the reactor and reacted with one another. The fats and oils were fed such that the LHSV became 0.8. The molar amount of methanol fed was 10 times as much as the molar amount of the fats and oils fed. The reaction pressure was 3.0 MPa·G, and the reaction temperature was 170° C. As a result of analysis of the resulting reaction products, the degree of formation of the methyl fatty ester in the oil phase was 97.3%, and the acid value of the oil phase was 1.1 (mg KOH/g).

Example 2

The oil phase obtained in the operation 2 in Example 1 was further reacted in the same reactor thereby giving an oil phase containing 99.4 wt % methyl fatty esters. Water was added in a final content of 2 wt % to the resulting oil phase, then stirred for 30 minutes and left for 1 hour to separate it into oil and aqueous phases, followed by rectification to give methyl fatty esters. Then, the resulting methyl fatty esters were subjected to hydrogenation reaction in a fixed bed reactor having a column packed with 259 mL titania-supported copper-zinc catalyst (in the form of a 3.2 mm⌀×3.2 mm cylinder with the composition: Cu=35%; Zn=1.8%; $TiO_2$ support, 50%) to give fatty alcohols. The hydrogenation reaction was conducted under the conditions of a pressure of 19.6 MPa and a temperature of 220° C. The feed rate of methyl fatty esters was 187 mL/h, and the flow rate of hydrogen was 414 NL/h.

As can be seen from the results in the Reference Examples, Examples and Comparative Example above, lower alcohols can be effectively recovered while the quality of alkyl fatty esters is secured according to the process of the invention.

That is, in the Examples in the present invention, alkyl fatty esters having a low acid value similar to that in Reference Example 1 not using recovered alcohol can be produced economically advantageous in higher yield. On the other hand, alkyl fatty esters of such low acid value as in the present invention cannot be obtained in the process in the Comparative Example wherein fats/oils and lower alcohols are fed together to the reactor at an upper stage and then sent to the reactor at lower stage.

The invention claimed is:

1. A process for producing alkyl fatty esters and glycerin from fats/oils and a C1 to C5 lower alcohol(s) by a multistage reaction process, which comprises a step of feeding liquid fats and oils to a reactor provided with a catalyst at an upper stage and sending them to a stage at a downstream side, while feeding a liquid lower alcohol to a reactor at a lower most stage and simultaneously returning a lower alcohol recovered from an outlet of the reactor to a stage at an upstream side, thereby repeating the reaction which further comprises steps of separating a lower alcohol(s) from reaction products comprising fats and oils obtained from the reactor at an upper stage and subjecting the resulting liquid component to oil/water separation to remove glycerin at a stage of the reactor between an upper stage and a lower stage wherein a stoichiometric quantity of lower alcohol in terms of a molar ratio of lower alcohol to fats and oils, calculated as triglycerides, is from 1.5 to 15, wherein the reaction is conducted at a temperature ranging from 60° C. to 200° C. and at a pressure ranging from 0.5 to 8 MPa, and wherein the degree of formation of said alkyl fatty ester is 86.9% or more.

2. The process of claim 1, wherein said catalyst has a strong acid point of not higher than 0.2 mmol/g-cat and weak acid point of not lower than 0.3 mmol/g-cat.

3. The process of claim 1, wherein said reaction is conducted continuously in a fixed bed reactor at a liquid hourly space velocity of said fats/oils of not lower than 0.02 /hr and not higher than 2.0 /hr.

4. The process of claim 1, wherein a direction of flow of liquid is downflow, said fats/oils are fed to a reactor at an uppermost stage.

5. The process of claim 1, wherein said reaction is conducted at a reaction temperature of 80° C. or more.

6. The process of claim 1, wherein said catalyst is a solid catalyst.

7. The process according to claim 6, wherein fixed-bed reactors each packed with said solid catalyst are used as the reactors.

8. The process according to claim 7, wherein the solid catalyst is a solid acid catalyst.

9. The process according to claim 8, wherein the solid acid catalyst is a molded product of a heterogeneous catalyst comprising aluminum orthophosphate.

10. The process of claim 1, wherein said reactor is a vessel type reactor and the reaction in said vessel type reactor is conducted for 2 to 10 hours.

* * * * *

UNITED STATES PATENT AND TRADEMARK OFFICE
CERTIFICATE OF CORRECTION

| | |
|---|---|
| PATENT NO. | : 8,501,974 B2 |
| APPLICATION NO. | : 12/158833 |
| DATED | : August 6, 2013 |
| INVENTOR(S) | : Wataru Nomura et al. |

It is certified that error appears in the above-identified patent and that said Letters Patent is hereby corrected as shown below:

On the title page, Item (86), the PCT Information is incorrect. Item (86) should read:

--(86) PCT No.:    PCT/JP2006/326329

§ 371 (c)(1),
(2), (4) Date:    Aug. 14, 2008--

Signed and Sealed this
First Day of October, 2013

Teresa Stanek Rea
*Deputy Director of the United States Patent and Trademark Office*